United States Patent [19]

Lindsay et al.

[11] 4,260,443
[45] Apr. 7, 1981

[54] LAMINATED ABSORBENT PROCESS

[75] Inventors: William F. Lindsay; Robert A. Meintrup, both of Muscatine, Iowa; Howard J. Slawny, Green Bay, Wis.

[73] Assignee: Grain Processing Corporation, Muscatine, Iowa

[21] Appl. No.: 953,039

[22] Filed: Oct. 20, 1978

[51] Int. Cl.³ .............................................. B32B 31/00
[52] U.S. Cl. .................................... 156/220; 128/284; 156/283; 156/284; 156/290; 428/198
[58] Field of Search ............... 428/156, 174, 195, 198, 428/206; 156/283, 284, 290, 291, 220

[56] References Cited

U.S. PATENT DOCUMENTS 4,117,184  9/1978  Erickson et al. ................... 418/224

FOREIGN PATENT DOCUMENTS 851686  9/1970  Canada.
893677  2/1972  Canada.
931030  7/1973  Canada.

Primary Examiner—James J. Bell
Attorney, Agent, or Firm—Neuman, Williams, Anderson & Olson

[57] ABSTRACT

A laminate of tissue-like materials having a liquid absorbing agent fixed in position between lamina.

4 Claims, 3 Drawing Figures

FIG. 1
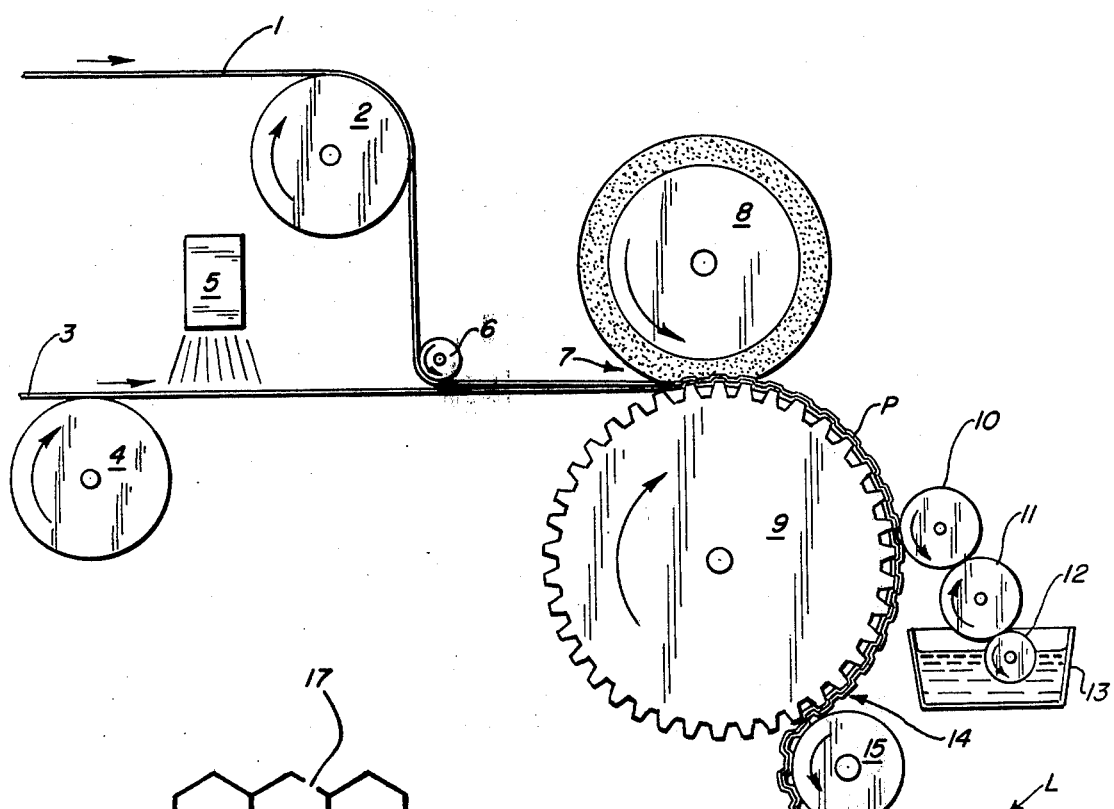
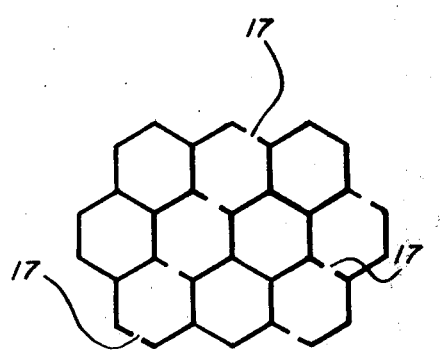
FIG. 3
FIG. 2
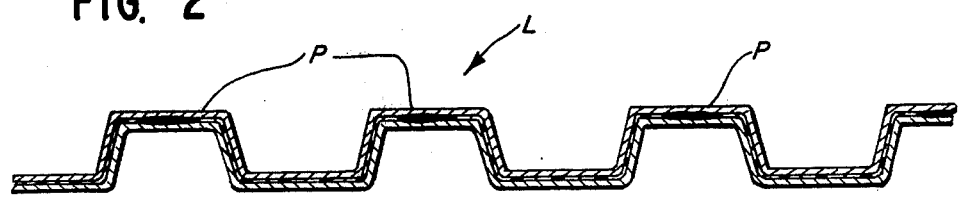

4,260,443

LAMINATED ABSORBENT PROCESS

The present invention relates to the production of a laminate of two or more layers of tissue-like material in such manner that fixed between the lamina is a layer of liquid absorbing agent in powder, flake or fiber form. The liquid absorbing agent is distributed between the layers and fixed in position so that migration of the agent between the layers is inhibited but, nevertheless, retains its ability to absorb liquid.

BACKGROUND OF THE INVENTION

Many types of disposable absorbent softgoods products are being used in the marketplace today. These products include disposable baby and adult diapers, underpads or hospital bed pads, catamenial devices and surgical dressings and wipes. Their main function is to absorb and retain fluids. These products are frequently constructed with a nonwoven cover sheet, an absorbent center section and a water impermeable backing sheet. The absorbent medium can be tissue wadding or fluff pulp fiber. To achieve the necessary absorbency with such products, large quantities of the absorbent medium are needed which results in a bulky finished product. There are several disadvantages resulting from the bulkiness of these products. For example, they require large amounts of space for storage, both by the producer and the distributors or user whether it is a retail establishment or a hospital; shipping costs are high due to the large volume per item; and in the case of diapers and catamenial devices, the bulkiness causes discomfort for the user.

In the last few years certain hydrocolloidal polymers have been developed which have the ability to absorb large quantities of liquids including, e.g., body fluids. The use of these polymers in disposable softgoods products offers advantages. When used in disposable softgoods products, these materials result in better absorbency thereby permitting reduction in the bulk of the disposable product by allowing the manufacturer to decrease the amount of cellulose wadding or fluff pulp in the disposable product. Also, since they generally possess greater affinity for liquid than does cellulosic material, these polymer materials retain the fluid better in a disposable product under pressure. Thus, disposable softgoods products containing the hydrocolloidal polymers show better performance when pressure is applied to them than is the case with the cellulosic product. This is exemplified when a patient lies on an underpad or a child sits or otheerwise places pressure on a disposable diaper.

However, there are problems related to the use of the hydrocolloid polymers in disposable products. For example, it has been found that when hydrocolloidal polymers, especially in powder form, are added to disposable softgoods, the polymers are dusty during application and sift in the finished product. The sifting of the hydrocolloidal particles takes place during the manufacture, handling, storage, and use of the article. This results in the particles sifting or migrating away from the useful portions of the finished disposable softgoods product. Also, when certain hydrocolloidal polymers have absorbed liquid they become slippery or slimy. This can cause premature failure of the product and also give an undesirable appearance and feel to the product in use. It is, therefore, advantageous to contain the liquid-absorbing polymer in the proper location in the finished disposable softgoods product.

SUMMARY OF INVENTION

It has been found that it is possible to overcome the problems associated with the use of large amounts of cellulosic material in disposable products and also the problems encountered with hydrocolloidal polymers in powder form by forming a laminated sheet composed of two or more layers of tissue with the water absorbing polymer fixed in place between the layers. More particularly, the fixing of the polymer is achieved by applying water at spaced points to superposed sheets to moisten water absorbing polymer and cause it to serve as an adhesive at those points. Thus, we use the liquid absorbing agent in a unique manner. First, it is employed as an adhesive after being moistened by a minor amount of water and thereafter it is substantially confined to provide maximum absorbability of liquid during diaper or other use.

In the practice of the invention according to the best mode currently known, the superimposed sheets are embossed to provide the points or "land" areas of adhesion. A wide variety of embossing patterns may be employed to advantage, particularly those that develop pocket-like spaces for confining the polymer. For example, embossed points or projections may be used although in this case there may be some movement of the polymer between the sheets which may not be desirable. Other patterns are more desirable especially if the pattern is made up of a discontinuous series of lines or curves which form broken or open circles, ovals, squares, rectangles, trapezoids, parallelograms, hexagons, octagons, stars and the like. Additional patterns can consist of closed designs that are slightly separated. Likewise, the pattern can be composed of a combination of two or more designs. The land area of the embossing pattern can range from a small percentage, e.g., about 1% up to about 50% of the tissue area.

DETAILED DESCRIPTION

The invention is described in conjunction with illustrated embodiments in the accompanying drawing, in which:

FIG. 1 is a schematic flow sheet illustrating a suitable arrangement of apparatus for producing the laminated product in accordance with the invention;

FIG. 2 is a cross-section of a laminated product in accordance with the invention; and FIG. 3 is a fragementary plan view of an embossing pattern advantageously employed in the practice of the invention.

In accordance with one preferred embodiment of the invention, a high-capacity liquid absorbing laminate is prepared by applying a metered amount of dry liquid absorbing agent between two plies of cellulosic tissue or other suitable material, introducing the combined web into an embossing nip comprised of an embossing roll and smooth rubber roll. After passing through the embossing nip, while the combined web is impressed on the embossing roll, a small amount of water is applied to all or a percentage of the embossed or raised area. By moistening the liquid absorbing agent at the embossed portions, it becomes tacky and acts as an adhesive at these locations to secure the tissue sheets together. The adhesion between the plies of tissue is sufficient to lock the bulk of the dry liquid absorbing agent into place, thus immobilizing the agent in the desired areas as well as supplying the liquid absorbing agent in a convenient, easy to use form for use in disposable softgoods products and other applications.

The materials used to form the laminate, i.e., the facing and backing sheets of the invention, are preferably cellulosic tissues with basis weights from 8 pounds per ream to 40 pounds per ream. Nonwoven fabrics and water permeable plastic materials can also be used, as well as combinations of materials such as tissue-tissue, nonwoven-tissue, tissue-plastic, nonwoven-plastic both permeable and water-impermeable and the like.

Liquid absorbing agents which exhibit adhesive properties when moistened with water can be advantageously utilized in accordance with this invention. Many such liquid absorbing agents are known to the art and include, for example, such materials as disclosed in U.S. Pat. Nos. 3,661,815 (Grain Processing Corporation's Polymer 35-A-100), 3,935,099 (USDA Super Slurper), 4,076,663 (Sanyo Chemical's Sanwet) and 4,090,013 (National Starch & Chemicals' Permasorb). Combinations of water absorbing agents can be employed with the amount of agent used being primarily dependent on the absorbency desired in the finished product. Preferred liquid absorbing agents are the alkali metal carboxylate salts of starch-polyacrylonitrile graft copolymers or starch-polymethacrylonitrile graft copolymers described in U.S. Pat. No. 3,661,815. Generally speaking, laminated products having good liquid absorbing properties, including body liquids such as urine, are obtained when these preferred liquid absorbing agents are employed in amounts from about 0.25 to 15 grams per square foot of laminate.

The laminate product can be produced using a variety of equipment. The drawing shows in schematic form one arrangement of apparatus for practicing this invention.

With specific reference to FIG. 1 of the drawings, an elongated sheet 1 of cellulosic tissue or the like is unwound from a parent roll (not shown) and passes over a conveying roll 2 and simultaneously a second sheet 3 passes over conveying roll 4. A water-absorbing agent is distributed on the surface of sheet 3 using a suitable distributing mechanism 5 such as a vibratory feeder. Sheets 1 and 3 are guided by conveying roller 6 into the nip 7 of rolls 8 and 9. Roll 8 is a rubber covered smooth roll while roll 9 is an engraved steel roll. Alternatively, matched steel or paper to steel embossing rolls may be employed.

The dry laminate L is characterized by a plurality of projections or raised portions P (see also FIG. 2) to which water is applied by means of water roll 10, which is fed water from pan 13 via rolls 11 and 12. By controlling the pressure between rolls 10, 11 and 12, and the speed of the rolls, the amount of water applied to the laminate L is suitably controlled. After the raised or embossed portions P of the laminate L are moistened, the laminate passes through the nip 14 of embossing roll 9 and a "marrying" roll 15. The embossed laminate L is then sent to finishing operations such as rewinding and/or packaging.

In the illustration given, the second sheet 3 may be a cellulosic tissue like sheet 1 or a variety of other flexible webs, even water-impermeable plastic inasmuch as water has only to penetrate sheet 1 to effect sheet adhesion.

The amount of water applied can vary according to the substrate used and the quantity of liquid-absorbing material present. It generally ranges from about 1% based on total finished laminate weight to approximately 15%. However, levels from 0.5% to 30% moisture, based on total laminate weight, can be utilized. The water applicating roll may vary in surface pattern to cover any suitable percentage of the embossed land area.

The following examples are illustrative of the invention.

EXAMPLE 1

Two layers of 20 pound per 3,000 square feet ream basis weight tissue at 6% moisture were used to form a laminate. Polymer 35-A-100, available commercially from Grain Processing Corporation, was distributed on one layer of the 20 pound tissue at a rate of one gram per square foot. Polymer 35-A-100 is an alkali metal carboxylate salt of a starch-acrylonitrile graft polymer in which the molar ratio of acrylonitrile to starch is greater than 2:1, which salt is produced by saponification with an aqueous alcoholic base solution as described in U.S. Pat. No. 3,661,815. An additional layer of 20 pound tissue was applied on top of the tissue polymer combination to form a laminate by being passed through the nip of an embossed steel roll and smooth rubber roll. The embossing roll was provided with an oval pattern and as a result of the embossing raised ovals were formed in the tissue web. The web then passed by a smooth rubber water metering roll which deposited moisture on the raised oval embossments causing the polymer to tack itself to the tissue layers at the embossed or raised portions. The resulting tissue product contained 7.5% moisture based on total laminate weight and exhibited soft hand characteristics. The liquid absorbing polymer was fixed within the non-embossed portions of the laminate.

EXAMPLE 2

Following the same procedure as above, additional laminates were made using two grams of polymer 35-A-100 per square foot of laminate. The finished product tissue moisture contained 9.65% and had very good absorbency, being nondusting.

Referring now to FIG. 3, a variation of embossing pattern is seen which is essentially a series of interlaced hexagons, viz., a honeycomb of 5—10 mm. across. This arrangement promotes confinement of the polymer. However, it may be advantageous in some instances to cut away a portion of the hexagon-defining wall as at 17 to permit relief of web stresses which otherwise might develop into wrinkles.

A feature of the present invention is that the liquid-absorbing agent can be used in roll form which is familiar to most converters of disposable softgood products and the problems of dusting and handling of a powdered material are eliminated. With the laminate of the invention, the liquid-absorbing agent is positioned and held in the proper location for maximum absorbency and fluid retention during the life of the disposable softgoods article. Quite importantly, the laminate has soft hand characteristics, thus, not adding to the "boardiness" of a disposable softgoods product. Further, the invention avoids the disadvantageous tendency of sheets to tear when merely mechanically bonded, viz., mechanical embossing alone permits the tissue to tear allowing the polymer to escape. Still further, the invention avoids certain disadvantages which arise if the tissue is moistened prior to addition of the polymer. Then, the tissue wrinkles and tears and is unacceptable from the standpoint of strength and machine runability. If the entire tissue is moistened after polymer application but before the laminate is embossed, the tissue is very susceptible to tearing which allows the polymer to escape. The polymer then sticks to the laminating rolls thereby causing the tissue to stick to the rolls. If the water is added to the tissue as a spray or in any manner that moistens all the tissue after it has passed through the laminating rolls, it is necessary to dry the tissue before it is wound on the rewind rolls. This is uneconomical and results in boardiness and poor runability of the laminate.

However, the invention avoids these disadvantages by utilizing the liquid absorbing agent in a novel and ingenious manner to effect different results at different times in the life span of the product—not only preventing agent sifting but also providing a product with soft "hand" characteristics because of the way the webs are integrated into a laminate.

While the present invention is described with reference to two sheets or lamina, it is apparent that multiple layers of tissue can be used in any combination of tissue-polymer-tissue, tissue-tissue-polymer-tissue-tissue, etc. in single or multiple plies as long as the water can be made to penetrate the tissue and moisten the absorbing agent to render it adhesive. Thus, those modifications and equivalents which fall within the spirit of the invention are to be considered a part thereof.

What is claimed is:

1. A process for producing a liquid absorbing laminated structure which comprises:
   (a) distributing in dry form onto a first sheet a liquid absorbing material which when moistened with water exhibits adhesive properties,
   (b) superimposing a second water-permeable sheet on said first sheet,
   (c) applying water at spaced points to said second sheet to moisten said liquid absorbing agent and cause it to serve as an adhesive at said points, and
   (d) then applying pressure to force together said sheets whereby a laminated structure is produced having the water absorbing agent distributed therein in substantially immobilized condition.

2. A process for producing a liquid absorbing laminated structure which comprises:
   (a) distributing in dry form onto a first sheet a liquid absorbing material which when moistened with water exhibits adhesive properties,
   (b) superimposing a second water-permeable sheet on said first sheet having the liquid absorbing agent distributed thereon,
   (c) embossing said superimposed sheets,
   (d) applying water to the embossed portions only of said sheets to moisten said liquid absorbing agent and cause it to serve as an adhesive at the location of said embossed portions, and
   (e) then applying pressure to force together said sheets whereby a laminated structure is produced having the water absorbing agent distributed therein in substantially immobilized condition.

3. A process for producing a liquid absorbing laminated structure which comprises:
   (a) distributing onto a first sheet a hydrocolloidal polymer material in dry form, said material when moistened with water exhibiting adhesive properties,
   (b) superimposing a second water-permeable sheet on said first sheet, said second sheet being a tissue web having a basis weight of from about 8 lbs. to about 40 lbs. per 3,000 square foot ream,
   (c) embossing said superimposed sheets to create land areas in said second sheet occupying from about 1% to about 50% of the surface thereof,
   (d) applying from about 0.5% to about 30% water based on the weight of said laminated structure to said land areas only to moisten said material and cause it to serve as an adhesive at the location of said land areas, and
   (e) then applying pressure to force together said sheets whereby a laminated structure is produced having the material distributed therein in substantially immobilized condition.

4. The process of claim 3 in which said land areas are sized and arranged to provide pockets to substantially confine discrete amounts of said polymer material.

* * * * *